United States Patent
Doi et al.

(10) Patent No.: US 6,479,556 B2
(45) Date of Patent: Nov. 12, 2002

(54) OPHTHALMIC COMPOSITIONS FOR SOFT CONTACT LENS, METHOD OF ENHANCING WETTABILITY OF SOFT CONTACT LENS AND METHOD OF INHIBITING TERPENOID ADSORPTION

(75) Inventors: Koji Doi, Kobe (JP); Hisayuki Nakayama, Nishinomiya (JP); Takuya Nakajima, Kobe (JP); Noriko Sakai, Nara (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/931,764

(22) Filed: Aug. 20, 2001

(65) Prior Publication Data

US 2002/0052419 A1 May 2, 2002

Related U.S. Application Data

(62) Division of application No. 09/486,212, filed as application No. PCT/JP98/03776 on Aug. 24, 1998.

(30) Foreign Application Priority Data

Aug. 26, 1997 (JP) .............................. 9-229775
Jul. 10, 1998 (JP) ........................... 10-195800

(51) Int. Cl.[7] .............................. A01N 31/00
(52) U.S. Cl. .................. 514/724; 514/912; 514/729
(58) Field of Search ................. 514/724, 729, 514/912

(56) References Cited

FOREIGN PATENT DOCUMENTS

| EP | 493320 | 7/1992 |
|---|---|---|
| JP | 48-37910 B | 11/1973 |
| JP | 52-109953 A | 9/1977 |
| JP | 4-338713 | 11/1992 |
| JP | 07-118147 A | 5/1995 |
| JP | 8-319323 | 12/1996 |
| WO | 96/06644 | 3/1996 |

*Primary Examiner*—Zohreh Fay
(74) *Attorney, Agent, or Firm*—Wenderoth, Lind & Ponack, L.L.P.

(57) ABSTRACT

The present invention provides an ophthalmic composition for soft contact lenses (SCL), which contains a terpenoid as an active ingredient, an ophthalmic composition for SCL, which contains polyoxyethylene sorbitan ester, a method of enhancing the wettability of soft contact lenses, which comprises bringing terpenoid into contact with SCL and a method of inhibiting adsorption of terpenoid onto SCL, which comprises adding polyoxyethylene sorbitan ester to an ophthalmic composition containing a terpenoid. The ophthalmic composition containing a terpenoid improves, for example, the wettability of SCL, thereby to inhibit decrease in the water content of SCL. As a result, it can inhibit a dry feeling and an uncomfortable feeling during wearing SCL and is useful for enhancing the wettability of SCL. Further, addition of polyoxyethylene sorbitan ester leads to the inhibition of adsorption of terpenoid onto SCL.

4 Claims, No Drawings

US 6,479,556 B2

OPHTHALMIC COMPOSITIONS FOR SOFT CONTACT LENS, METHOD OF ENHANCING WETTABILITY OF SOFT CONTACT LENS AND METHOD OF INHIBITING TERPENOID ADSORPTION

This application is a division application of Ser. No. 09/486,212 filed Feb. 24, 2000, which is a 371 of PCT/JP98/03776, filed Aug. 24, 1998.

TECHNICAL FIELD

The present invention relates to an ophthalmic composition for soft contact lenses (hereinafter to be abbreviated as SCL). More particularly, the present invention relates to a composition for enhancing the wettability of SCL, a method of enhancing the wettability of SCL and a method of inhibiting adsorption of terpenoid onto SCL.

BACKGROUND ART

SCL usually contains water and causes less uncomfortable feeling. However, a long-term use of the lens often causes a dry feeling. This is because when the water contained in the lens evaporates, precorneal tear film under SCL is affected and corneal stain occurs, and further, when the water content decreases, the curve of SCL and the like changes to have a different lens standard. As a result, an uncomfortable feeling is enhanced.

A dry feeling and an uncomfortable feeling due to lower water content are peculiar to SCL, and there is a demand for the solution to this problem of SCL.

It is therefore an object of the present invention to provide an ophthalmic composition for SCL, such as a composition capable of inhibiting a dry feeling, and an uncomfortable feeling caused by a decreased water content of SCL.

Another object of the present invention is to provide a method of enhancing the wettability of SCL.

DISCLOSURE OF THE INVENTION

The present inventors have conducted intensive studies in an attempt to achieve the above-mentioned objects and found that terpenoid can improve the wettability of SCL, thus inhibiting a decrease in the water content of SCL to eventually inhibit a dry feeling and an uncomfortable feeling, which resulted in the completion of the present invention.

Accordingly, the present invention provides the following.

(1) An ophthalmic composition for SCL, which contains a terpenoid as an active ingredient.
(2) The ophthalmic composition of (1) above, which is for enhancing the wettability of SCL.
(3) The ophthalmic composition of (1) or (2) above, wherein the terpenoid is at least one member selected from the group consisting of menthol, borneol and camphor.
(4) The ophthalmic composition of any of (1) to (3) above, which is in the form of an eye drop.
(5) The ophthalmic composition of any of (1) to (4) above, which contains polyoxyethylene sorbitan ester and which is in the form of a liquid when in use.
(6) The ophthalmic composition of any of (1) to (5) above, which is in the form of a liquid having a pH of not less than 5.5 when in use.
(7) A method of enhancing the wettability of SCL, which comprises bringing a terpenoid into contact with the SCL.
(8) The method of (7) above, wherein the terpenoid is at least one member selected from the group consisting of menthol, borneol and camphor.
(9) A method of inhibiting adsorption of terpenoid onto SCL, which comprises adding polyoxyethylene sorbitan ester to an ophthalmic composition which contains a terpenoid and which is in the form of a liquid when in use.
(10) A method of inhibiting adsorption of terpenoid onto SCL, which comprises adjusting a pH of an ophthalmic composition which contains a terpenoid and which is in the form of a liquid when in use, to not less than 5.5.
(11) The method of enhancing the wettability of SCL of (9) or (10) above, wherein the terpenoid is at least one member selected from the group consisting of menthol, borneol and camphor.

The terpenoid to be contained in the ophthalmic composition for SCL of the present invention may be a monoterepene such as menthol, borneol, camphor, geraniol, cineole, anethol, limonene, eugenol and the like, a sesquiterpene such as farnesol, nerolidol and the like, a diterpene such as phytol, cembrene and the like, or other terpenoid. Particularly preferred are menthol, borneol, camphor and the like.

The content of the terpenoid to be contained in the ophthalmic composition for SCL of the present invention is 0.0001–0.2 (W/V) %, preferably 0.001–0.05 (W/V) %, when in use.

The ophthalmic composition for SCL of the present invention, which contains a terpenoid, can be used as a composition for any ophthalmic use for SCL. To be specific, it can be used as a composition for enhancing the wettability of SCL, and the like.

The ophthalmic composition for SCL of the present invention can be used in any form of a preparation generally used for topical application to the eye. For example, it may be prepared into an eye drop, eye ointment, gel, solid preparation that becomes a liquid upon dissolution when in use (e.g., tablet, powder, granule, freeze-dry preparation and the like), and the like, with preference given to use in the form of an eye drop. The eye drop may be aqueous or non-aqueous, and may be a solution or suspension.

The SCL worn on an eye is washed with a tear fluid. Even if an ingredient of the ophthalmic composition is adsorbed onto SCL, it is normally washed away and rarely causes irritation to the eye, and the like. However, the adsorption of each ingredient is desirably as small as possible.

From this viewpoint, the present inventors have conducted various studies and found that (1) addition of polyoxyethylene sorbitan ester to an ophthalmic composition for SCL, which contains a terpenoid as an active ingredient, and which becomes a liquid upon dissolution when in use, and/or (2) adjustment of pH to not less than 5.5 when in use result(s) in the inhibition of adsorption of terpenoid onto SCL.

Accordingly, the present invention relates to an ophthalmic composition for SCL, which contains a terpenoid as an active ingredient and which becomes a liquid upon dissolution when in use, and provides (1) a composition containing polyoxyethylene sorbitan ester and/or
(2) a composition having a pH of not less than 5.5 when in use.

From a different aspect, the present invention provides the following.

(1) A method of inhibiting adsorption of terpenoid onto SCL, which comprises adding polyoxyethylene sorbitan ester to an ophthalmic composition which contains a terpenoid and which becomes a liquid upon dissolution when in use.
(2) A method of inhibiting adsorption of terpenoid onto SCL, which comprises adjusting a pH when in use of an ophthalmic composition, which contains a terpenoid and which becomes a liquid upon dissolution when in use, to not less than 5.5.

The ophthalmic composition for SCL of the present invention improves, for example, the wettability of SCL, thereby to inhibit a decrease in the water content of SCL. As a result, it can inhibit a dry feeling and an uncomfortable feeling during wearing SCL and is useful for enhancing the wettability of SCL.

In addition, (1) an ophthalmic composition which contains polyoxyethylene sorbitan ester and which becomes a liquid upon dissolution when in use and (2) an ophthalmic composition which has an adjusted pH of not less than 5.5 and which becomes a liquid upon dissolution when in use, are associated with less concern of irritation to the eye or an adverse influence such as cloudiness of SCL and the like, since adsorption of terpenoid onto SCL is inhibited.

It is preferable that polyoxyethylene sorbitan ester be added to the concentration when in use of 0.01–0.5 (W/V) %, preferably 0.05–0.2 (W/V) %.

Examples of preferable polyoxyethylene sorbitan ester include polysorbate 80, polysorbates 20, 40, 60, 65, 85 and the like.

The inventive composition is adjusted to have a pH when in use of not less than 5.5, preferably not less than 5.5 and not more than 8. In this way, the adsorption of terpenoid onto SCL can be inhibited. When the pH is not less than 5.5, terpenoid is hardly adsorbed onto SCL. When the pH is not less than 8, the composition becomes strongly alkaline and is not preferable as an ophthalmic composition.

The pH is adjusted using a pH adjusting agent. Examples of the pH adjusting agent include hydrochloric acid, citric acid and a salt thereof (sodium citrate, sodium dihydrogencitrate and the like), phosphoric acid and a salt thereof (disodium hydrogenphosphate, potassium dihydrogenphosphate and the like), acetic acid and a salt thereof (sodium acetate, ammonium acetate and the like), tartaric acid and a salt thereof (sodium tartrate and the like), sodium hydroxide, potassium hydroxide, sodium carbonate, sodium hydrogencarbonate, boric acid and a salt thereof (sodium borate) and the like.

The ophthalmic composition for SCL of the present invention can be prepared by adding a terpenoid and a base (e.g., solvent, ointment base and the like), and further adding, according to the dosage form, various additives such as a solubilizer, buffer, isotonicity agent, preservative, stabilizer, thickener, adsorption inhibitor, chelating agent, pH adjusting agent, suspending agent and the like, as appropriate, and following a known method.

Examples of solvent as a base include water (e.g., distilled water, sterile purified water, physiological saline and the like), alcohols (e.g., ethanol, propylene glycol, macrogol, glycerol and the like) and the like.

Examples of solubilizer include polyvinylpyrrolidone, polyethylene glycol, propylene glycol, polyoxyethylene hydrogenated castor oil 60, polyaryl 40 stearate and the like.

A buffer is used to make the pH of the inventive ophthalmic composition for SCL approximately 5–9, preferably 6–8. For example, used are boric acid or a salt thereof (sodium borate and the like), citric acid or a salt thereof (sodium citrate and the like), tartaric acid or a salt thereof (sodium tartrate and the like), gluconic acid or a salt thereof (sodium gluconate and the like), acetic acid or a salt thereof (sodium acetate and the like), phosphoric acid or a salt thereof (sodium hydrogenphosphate, sodium dihydrogenphosphate and the like), various amino acids and the like or a combination thereof.

The isotonicity agent may be, for example, sorbitol, glucose, mannitol, glycerol, propylene glycol, sodium chloride, potassium chloride and the like.

Examples of preservative include p-hydroxybenzoates, benzalkonium chloride, benzetonium chloride, chlorobutanol, benzyl alcohol, sorbic acid or a salt thereof, chlorhexidine gluconate, sodium dehydroacetate, cethylpyridinium chloride, alkyldiaminoethylglycine hydrochloride and the like.

Examples of stabilizer include ascorbic acid, sodium edetate, cyclodextrin, condensed phosphoric acid or a salt thereof, sulfite, citric acid or a salt thereof and the like.

Examples of thickener include methylcellulose, hydroxyethylcellulose, hydroxypropylcellulose, hydroxypropylmethylcellulose, sodium chondroitin sulfate, sodium carboxymethylcellulose, polyvinylpyrrolidone, polyvinyl alcohol, polyethylene glycol and the like.

Examples of chelating agent include sodium edetate, sodium citrate, condensed phosphoric acid or a salt thereof (condensed sodium phosphate and the like) and the like.

Examples of suspending agent include methylcellulose, hydroxypropylcellulose, polyvinylpyrrolidone, polyoxyethylene hydrogenated castor oil 60, polyoxyl 40 stearate, polyethylene glycol, sodium carboxymethylcellulose, polyvinyl alcohol and the like.

As long as the object of the present invention is not impaired, the inventive ophthalmic composition for SCL may further contain an efficacious ingredient such as vitamins (e.g., retinol palmitate, pyridoxine hydrochloride, tocopherol acetate and the like), angiotonic (e.g., naphazoline hydrochloride, tetrahydrozoline hydrochloride and the like), antiinflammatory agent (e.g., dipotassium glycyrrhizinate, sodium azulenesulfonate and the like), and the like as appropriate.

The dose of the ophthalmic composition for SCL of the present invention when used as an eye drop to an adult, which contains a terpenoid as an active ingredient in 0.0001–0.2 (W/V) %, preferably 0.001–0.05 (W/V) %, is preferably 2 or 3 drops per administration which is given 5 or 6 times a day.

EXAMPLES

The present invention is explained in more detail in the following by way of Examples and Experimental Examples to demonstrate the effect of the present invention, which Examples are for the purpose of exemplification only, and do not limit the present invention in any way.

Example 1

An eye drop of the following recipe was prepared according to a conventional method.

| | |
|---|---|
| potassium chloride | 0.15 g |
| sodium chloride | 0.55 g |
| boric acid | 0.5 g |
| sodium borate | 0.55 g |
| sorbic acid | 0.1 g |
| sodium edetate | 0.01 g |
| 1-menthol | 0.002 g |
| hydroxyethylcellulose | 0.1 g |
| polysorbate 80 | 0.15 g |
| sterile purified water | appropriate amount |
| total amount | 100 ml (pH 7.3) |

Example 2

An eye drop of the following recipe was prepared according to a conventional method.

| | |
|---|---|
| potassium chloride | 0.15 g |
| sodium chloride | 0.55 g |
| boric acid | 0.5 g |
| chlorhexidine gluconate solution (20 W/V %) | 0.025 ml |
| (0.005 g as chlorhexidine gluconate) | |
| sodium edetate | 0.01 g |
| 1-menthol | 0.002 g |
| hydroxyethylcellulose | 0.1 g |
| polysorbate 80 | 0.15 g |
| sterile purified water | appropriate amount |
| sodium hydroxide | appropriate amount |
| total amount | 100 ml (pH 7.3) |

Example 3

An eye drop of the following recipe was prepared according to a conventional method.

| | |
|---|---|
| potassium chloride | 0.15 g |
| sodium chloride | 0.55 g |
| boric acid | 0.5 g |
| chlorhexidine gluconate solution (20 W/V %) | 0.025 ml |
| (0.005 g as chlorhexidine gluconate) | |
| sodium edetate | 0.01 g |
| 1-menthol | 0.002 g |
| hydroxyethylcellulose | 0.1 g |
| polysorbate 80 | 0.15 g |
| boric acid | 0.05 g |
| sterile purified water | appropriate amount |
| total amount | 100 ml (pH 7.3) |

Experimental Example 1

Wettability Test

Test solutions of the following recipes were prepared.

Test solution A:

| | |
|---|---|
| polysorbate 80 | 1 g |
| 1-menthol | 0.2 g |
| sterile purified water | appropriate amount |
| total amount | 100 ml |

Test solution B:

| | |
|---|---|
| polysorbate 80 | 1 g |
| sterile purified water | appropriate amount |
| total amount | 100 ml |

The above-mentioned Test solution A and Test solution B were respectively dropped onto the following-SCL (one lens) previously dried, and an angle formed by the droplet with the surface of the SCL at the part in contact with the surface was measured at the beam using a contact angle measuring device [ERMA Goniometer type Contact Anglemeter, M-2010A-A (manufactured by ERMA)] to give a contact angle.
(SCL used)
SCL (No. 1)
Main material: methyl methacrylate+N-vinylpyrrolidone
SCL (No. 2)
Main material: methyl methacrylate+glyceryl methacrylate The obtained angles of contact are shown in Table 1.

TABLE 1

| | angle of contact | |
|---|---|---|
| | SCL (No. 1) | SCL (No. 2) |
| Test solution A | 17° | 31° |
| Test solution B | 23° | 44° |

The angles of contact were smaller when the test solutions containing l-menthol were dropped onto SCLs No. 1 and No. 2. The results reveal that the addition of a terpenoid could improve the wettability of SCL.

Experimental Example 2

Inhibition of Dry Feeling and Uncomfortable Feeling

Two or three drops of the eye drop obtained in Example 1 were instilled into either eye of the test subjects (8 persons) wearing SCL, and 2 or 3 drops of the Test solution C of the following formula were instilled into the other eye. The respective eyes were examined for changes in a dry feeling and an uncomfortable feeling due to SCL.

A test solution of the following recipe was prepared according to a conventional method and used as Test solution C.

| | |
|---|---|
| potassium chloride | 0.15 g |
| sodium chloride | 0.55 g |
| boric acid | 0.5 g |
| sodium borate | 0.55 g |
| sorbic acid | 0.1 g |
| sodium edetate | 0.01 g |
| hydroxyethylcellulose | 0.1 g |
| polysorbate 80 | 0.15 g |
| sterile purified water | appropriate amount |
| total amount | 100 ml (pH 7.3) |

The obtained results were evaluated by giving points as mentioned below. The results with regard to dry feeling are shown in Table 2, and the results with regard to uncomfortable feeling are shown in Table 3.

Evaluation Method 5 points: The dry feeling or uncomfortable feeling vanished.

4 points: The dry feeling or uncomfortable feeling almost vanished.

3 points: The dry feeling and uncomfortable feeling did not change.

2 points: The dry feeling or uncomfortable feeling became rather severe.

1 point: The dry feeling or uncomfortable feeling became severe.

TABLE 2 dry feeling

| Test subject | Administration of eye drop of Example 1 | Administration of Test solution C |
|---|---|---|
| No. 1 | 4 | 2 |
| No. 2 | 5 | 3 |
| No. 3 | 4 | 3 |
| No. 4 | 5 | 3 |
| No. 5 | 5 | 3 |
| No. 6 | 4 | 4 |
| No. 7 | 4 | 3 |
| No. 8 | 5 | 3 |

TABLE 3 uncomfortable feeling

| Test subject | Administration of eye drop of Example 1 | Administration of Test solution C |
|---|---|---|
| No. 1 | 4 | 3 |
| No. 2 | 5 | 3 |
| No. 3 | 4 | 3 |
| No. 4 | 4 | 4 |
| No. 5 | 4 | 3 |
| No. 6 | 5 | 3 |
| No. 7 | 5 | 3 |
| No. 8 | 4 | 3 |

Experimental Example 3

Inhibition of Absorption of Terpenoid onto SCL

Test solutions of the following recipes were prepared.

Test Solution A

| l-menthol | 0.002 g |
|---|---|
| polysorbate 80 | 0.15 ml |
| sterile purified water | appropriate amount |
| total amount | 100 ml |

Test Solution B

| l-menthol | 0.002 g |
|---|---|
| sterile purified water | appropriate amount |
| total amount | 100 ml |

The above-mentioned Test solution A and Test solution B were respectively measured by precisely 4 ml in vials and SCL (two SCLS) were immersed therein. A solution into which SCL was not immersed was used as a control test solution. The solutions were shaken at room temperature for 14 hours and the content of l-menthol was measured. The difference from the control test solution was taken as the amount of adsorption onto SCL. l-Menthol was extracted with chloroform and quantitatively assayed by gas chromatography.

(SCL used)

Main material: hydroxyethyl methacrylate+methacrylic acid

The obtained results are as shown in Table 4.

The values in the Table are the total of the two SCLS.

TABLE 4

| Test solution A | 3.9 μg/lens |
|---|---|
| Test solution B | 5.9 μg/lens |

The eye instilled with the eye drop of Example 1 was free of the dry feeling and uncomfortable feeling due to SCL, but the eye instilled with Test solution C without terpenoid showed almost no changes.

The results reveal that the use of the ophthalmic composition containing a terpenoid of the present invention could suppress the dry feeling and uncomfortable feeling due to SCL.

The composition containing polyoxyethylene sorbitan ester showed suppressed adsorption of terpenoid onto SCL.

Experimental Example 4

Test of Influence of Osmotic Pressure and pH

Test solutions of the following recipes were prepared.

Test Solution A

| l-menthol | 0.002 g |
|---|---|
| sodium phosphate $2H_2O$ | 0.5 g |
| sodium hydroxide or hydrochloric acid | appropriate amount |
| sterile purified water | appropriate amount |
| total amount | 100 ml (pH 4.5) |

Test Solution B

| l-menthol | 0.002 g |
|---|---|
| sodium phosphate $2H_2O$ | 0.5 g |
| sodium hydroxide or hydrochloric acid | appropriate amount |
| sterile purified water | appropriate amount |
| total amount | 100 ml (pH 5.5) |

Test Solution C

| l-menthol | 0.002 g |
|---|---|
| sodium phosphate $2H_2O$ | 0.5 g |
| sodium hydroxide or hydrochloric acid | appropriate amount |
| sterile purified water | appropriate amount |
| total amount | 100 ml (pH 6) |

Test Solution D

| l-menthol | 0.002 g |
|---|---|
| sodium phosphate $2H_2O$ | 0.5 g |
| sodium hydroxide or hydrochloric acid | appropriate amount |
| sterile purified water | appropriate amount |
| total amount | 100 ml (pH 7) |

Test Solution E

| | |
|---|---|
| l-menthol | 0.002 g |
| sodium phosphate 12H$_2$O | 0.5 g |
| sodium hydroxide or hydrochloric acid | appropriate amount |
| sterile purified water | appropriate amount |
| total amount | 100 ml (pH 8) |

The above recipes were respectively measured by precisely 2.5 ml in vials and two SCLs were immersed therein. A solution, into which SCL was not immersed, was used as a control test solution. The solutions were shaken at room temperature for 38 hours and l-menthol was extracted with chloroform and quantitatively assayed by gas chromatography.

(SCL used)

Main material: hydroxyethyl methacrylate+methacrylic acid

Water content: 58.0%

The obtained results are as shown in Table 5.

The values in the Table are the total of the two SCLs.

TABLE 5

| | |
|---|---|
| Test solution A (pH 4.5) | 9.5 μg/lens |
| Test solution B (pH 5.5) | 7.3 μg/lens |
| Test solution C (pH 6) | 7.1 μg/lens |
| Test solution D (pH 7) | 7.3 μg/lens |
| Test solution E (pH 8) | 6.3 μg/lens |

Industrial Applicability

The ophthalmic composition for SCL of the present invention improves, for example, the wettability of SCL, thereby to inhibit decrease in the water content of SCL. As a result, it can inhibit a dry feeling and an uncomfortable feeling during wearing SCL and is useful for enhancing the wettability of SCL.

In addition, (1) an ophthalmic composition which contains polyoxyethylene sorbitan ester and which becomes a liquid when in use and (2) an ophthalmic composition which has an adjusted pH of not less than 5.5 and which becomes a liquid when in use, are associated with less concern of irritation to the eye and an adverse influence such as cloudiness of SCL and the like, since adsorption of terpenoid onto SCL is inhibited This application is based on application Nos. 229775/1997 and 195800/1998 filed in Japan, the contents of which are incorporated hereinto by reference.

What is claimed is:

1. A method of enhancing the wettability of a soft contact lens, which comprises bringing a solution comprising a terpenoid into contact with the soft contact lens.

2. The method of claim 1, wherein said terpenoid is a monoterpene.

3. The method of claim 2, wherein said monoterpene is at least one member selected from the group consisting of menthol, borneol and camphor.

4. The method of claim 1, wherein said terpenoid is contained at a concentration ranging from 0.0001 to 0.2 (w/v) %.

* * * * *